(12) United States Patent
Weyl et al.

(10) Patent No.: US 7,810,375 B2
(45) Date of Patent: Oct. 12, 2010

(54) SENSOR

(75) Inventors: Helmut Weyl, Wiesbaden (DE); Stefan Heinzelmann, Kernen (DE); Bastian Buchholz, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 516 days.

(21) Appl. No.: 11/632,330

(22) PCT Filed: May 10, 2005

(86) PCT No.: PCT/EP2005/052103

§ 371 (c)(1),
(2), (4) Date: Jun. 26, 2007

(87) PCT Pub. No.: WO2006/005641

PCT Pub. Date: Jan. 19, 2006

(65) Prior Publication Data

US 2007/0261473 A1 Nov. 15, 2007

(30) Foreign Application Priority Data

Jul. 14, 2004 (DE) .................. 10 2004 033 958

(51) Int. Cl.
*G01N 27/26* (2006.01)
*G01N 7/00* (2006.01)
(52) U.S. Cl. .................. 73/23.31; 73/31.05
(58) Field of Classification Search ............... 73/23.31, 73/23.32, 23.2, 31.05
See application file for complete search history.

(56) References Cited

U.S. PATENT DOCUMENTS 5,246,562 A * 9/1993 Weyl et al. ................. 204/424
5,821,401 A * 10/1998 Awarzamani et al. ....... 73/23.32
5,880,353 A * 3/1999 Graser et al. ................. 73/23.2
5,942,092 A * 8/1999 Weyl et al. .................. 204/424
6,164,120 A * 12/2000 Friese et al. ................. 73/23.2
6,206,377 B1 * 3/2001 Weyl ......................... 277/317
6,214,186 B1 * 4/2001 Watanabe et al. ........... 204/428
6,672,132 B1 * 1/2004 Weyl et al. ................. 73/23.31
6,762,671 B2 * 7/2004 Nelson ........................ 338/25
2001/0045120 A1 * 11/2001 Friese et al. ............... 73/23.31

(Continued)

FOREIGN PATENT DOCUMENTS

DE 196 28 423 9/1997

(Continued)

*Primary Examiner*—Lisa M Caputo
*Assistant Examiner*—Punam Roy
(74) *Attorney, Agent, or Firm*—Kenyon & Kenyon LLP

(57) ABSTRACT

A sensor, in particular a gas sensor for determining a physical characteristic of a measuring gas, in particular the temperature of the concentration of a gas component, in particular in the exhaust gas of an internal combustion engine, includes a sensor element which protrudes with a gas-side end section from a sensor housing and having a double protecting tube, which encloses the gas-side end section, and has an outer tube and an inner tube. For improved protection of the sensor element against thermal shock, a reduction in the heating power for the sensor element, and sufficiently high dynamics of the sensor, a cup-shaped central protecting tube is placed over the gas-side end section, the central protecting tube being provided with gas passage apertures in the tube casing, the gas passage apertures being positioned offset to the tube bottom with respect to the gas passage apertures present in the inner tube.

16 Claims, 1 Drawing Sheet

U.S. PATENT DOCUMENTS

2002/0148279 A1* 10/2002 Weyl et al. .................. 73/31.05
2004/0035700 A1* 2/2004 Taguchi et al. .............. 204/429

FOREIGN PATENT DOCUMENTS

| | | |
|---|---|---|
| DE | 196 48 685 | 5/1998 |
| DE | 101 53 735 | 5/2003 |
| EP | 0 974 836 | 1/2000 |
| EP | 1391724 A1 * | 2/2004 |
| JP | 53-061395 | 6/1978 |
| JP | 58-101166 | 7/1983 |
| JP | 7-027737 | 1/1995 |
| JP | 9-145668 | 6/1997 |
| JP | 10-508384 | 8/1998 |
| JP | 2000-088795 | 3/2000 |
| JP | 2004-157111 | 6/2004 |
| WO | WO 2005031334 A1 * | 4/2005 |

* cited by examiner

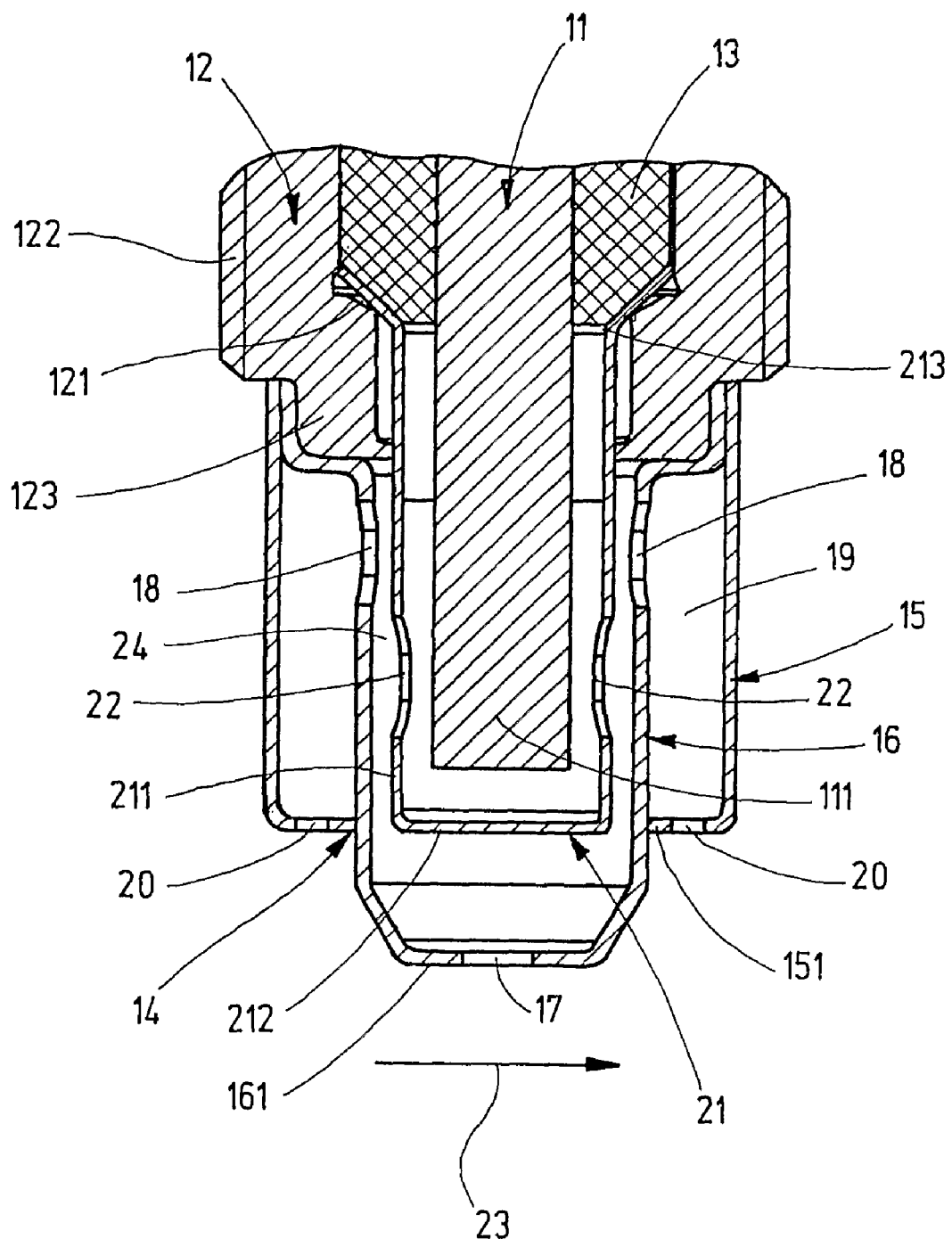

SENSOR

FIELD OF THE INVENTION

The present invention is directed to a sensor, in particular a gas sensor for determining a physical property of a measuring gas, in particular the temperature or the concentration of a gas component, in particular in the exhaust gas of an internal combustion engine.

BACKGROUND INFORMATION

For example, such sensors are used as lambda sensors for determining the oxygen concentration in the exhaust gas of an internal combustion engine. The sensor is provided with an integrated electrical heater in order to bring the gas-sensitive sensor element up to its operating temperature as quickly as possible, i.e., during the warm-up phase of the engine. The sensor element is made of ceramic materials. However, such ceramics are very sensitive to wide temperature fluctuations which result in cracks in the ceramic and bring about malfunctions and even total failure of the sensor. Extreme temperature fluctuations, also referred to as thermal shocks, occur on the surface of the sensor element, e.g., at start or during the warm-up phase of the internal combustion engine, when cold drops of water impact the already heated sensor element. Such drops of water may be formed when, during the warm-up phase, water vapor generated by the engine combustion condenses on cold surfaces of the exhaust system and the sensor, and when drops of water separate from the condensate film which are then entrained by the gas flow thereby reaching the sensor element.

For protecting the sensor element from the impact of droplets of water entrained by the exhaust gas flow, a double protecting tube is provided in a known sensor, used as an exhaust gas sensor (German patent document DE 199 24 319 C2), the double protecting tube, made up of an inner tube and an outer tube which each have gas inlet and outlet apertures, enclosing the section of the sensor element which is exposed to the exhaust gas. At least one inlet aperture of the inner tube and/or at least one inlet aperture of the outer tube, a flow element is situated which redirects the exhaust gas flow, which enters the space enclosed by the inner and outer tubes and/or the interior of the inner tube, toward the particular inner lateral surface of the inner and/or outer tube. The water is thus held on the inner lateral surfaces of the tubes and vaporizes slowly due to the exhaust gas temperature which rises during the increasing warm-up of the engine.

SUMMARY OF THE INVENTION

The sensor according to the exemplary embodiment and/or exemplary method of the present invention has the advantage that, by providing the central protecting tube within the double protecting tube, improved protection of the sensor element is achieved without affecting the dynamics of the gas sensor with regard to temperature fluctuations in the measuring gas. The additional central protecting tube, which is directly placed over the end section of the sensor element on the measuring gas side, offers reliable protection against thermal shock due to contact with water and reduces the heat losses on the heated sensor element occurring due to heat radiation and convection toward the measuring gas, so that the sensor reaches its operating temperature very quickly after being switched on and reliably maintains the operating temperature under all operating conditions.

Additionally, the reduced heat loss lowers the heating power demand of the sensor. Due to the measuring gas flow in the double protecting tube and in the space between the inner tube and the central protecting tube achieved by using the central protecting tube and due to the separation edges formed by the gas passage apertures in the central protecting tube, good turbulence of the measuring gas around the section of the sensor element on the measuring gas side is achieved which, together with the pulsation of the measuring gas, which typically occurs in the exhaust gas of internal combustion engines, causes a rapid exchange of the measuring gas in the interior of the central protecting tube.

Due to improved protection of the sensor element achieved by using the central protecting tube, the gas passage apertures in the double protecting tube may be designed to be larger so that they are not clogged by depositing particulates, e.g., soot. The particulates passing through the gas passage apertures in the double protecting tube are combusted on the hot tube casing of the central protecting tube since it is quickly heated to a temperature sufficient for the combustion process of these particulates due to the proximity to the heated sensor element and its rather thin wall. This improves the overall service life and dynamics of the sensor which are retained even under difficult operating conditions such as an individual cylinder regulation, for example.

The sensor according to the exemplary embodiment and/or exemplary method of the present invention may advantageously be used as a lambda sensor in internal combustion engines in which great temperature differences occur between idling and full load and the sensor must be installed in the exhaust pipe displaced back from the hot exhaust gas flow for reasons of overheating. Despite the associated longer heating time of the sensor housing after the cold start and the associated sometimes extended period during which the dew point is not exceeded on the housing mass during longer idling phases and at low outside temperatures, the sensor element is effectively protected.

Advantageous refinements of and improvements on the sensor described herein are provided by the further measures described herein.

According to an exemplary embodiment of the present invention, the protruding end of the inner tube of the double protecting tube is conically tapered like a cone frustum and sealed by a tube bottom, while the outer tube rests on the inner tube via a ring-shaped bottom part. The tube bottom of the inner tube has a front hole, and the ring-shaped bottom part or bottom ring has multiple gas passage apertures which are situated offset with respect to one another in the circumferential direction. Due to this constructive measure, a clearly improved measuring gas flow in the double protecting tube and between the inner tube of the double protecting tube and the central protecting tube is achieved, which causes optimal turbulence of the measuring gas within the central protecting tube.

According to an exemplary embodiment of the present invention, the central protecting tube is designed to have a very thin wall, so that it has only a low specific heat which does not affect the sensor's dynamics.

BRIEF DESCRIPTION OF THE DRAWING

The FIGURE schematically shows a cross section of a lambda sensor for an internal combustion engine, in particular for an internal combustion engine of a motor vehicle.

DETAILED DESCRIPTION

A three-way catalytic converter having a lambda regulation is used for reducing the exhaust emission of internal combustion engines. The lambda sensor illustrated in FIG. 1 in a schematic cross section is used for controlling the air/fuel mixture in order to set a mixture as close to the stoichiometric ratio as possible by measuring the oxygen content in the exhaust gas, so that the harmful emissions are minimized due to optimum combustion. This lambda sensor is described in the following as an exemplary embodiment for a general sensor used as a gas sensor with which a physical property of a measuring gas, e.g., the temperature of the measuring gas or the concentration of a gas component in the measuring gas, is measured.

The lambda sensor has a sensor element 11 made of a ceramic material including an end section 111 on the gas side exposed to the exhaust gas and an end section (not shown) on the connection side in which electrical contacting of sensor element 11 is established for connection to a control unit and an analyzer unit. Sensor element 11 is accommodated in a sensor housing 12, of which only the end section on the gas side is shown in FIG. 1. A housing shoulder 121 is formed in the gas-side end section in the interior of sensor housing 12 by reducing the diametral clearance of sensor housing 12. Using a ceramic seal 13, which encloses sensor element 11 without a gap, sensor element 11 is inserted into sensor housing 12 in a gas-tight manner and protrudes with the gas-side end section from sensor housing 12. Sensor housing 12 is provided with an external thread section 122 with which the lambda sensor is screwed into a fitting, held on an exhaust pipe of the internal combustion engine at the place of installation, in such a way that measuring gas-side end section 111 immerses in the exhaust gas flowing in the exhaust pipe.

Gas side end section 111 of sensor element 11 is enclosed by a double protecting tube 14 which is pushed onto a housing flange 123, formed on sensor housing 12, and welded to it in a gas-tight manner. Double protecting tube 14 is made up of an outer tube 15 and an inner tube 16 which is concentrically enclosed with a radial clearance by outer tube 15 and protrudes beyond the free end of outer tube 15. The protruding end is conically tapered and sealed by a tube bottom 161 which is in one piece with inner tube 16. A central front hole 17 is introduced into tube bottom 161 and gas passage apertures 18 are provided in the tube wall close to the end of inner tube 16 facing away from tube bottom 161. Gas passage apertures 18 are situated on a circumference which may have equidistant spacing so that a circumferential ring of gas passage apertures 18 is created. Outer tube 15 rests on inner tube 16 via a bottom ring 151 which is in one piece with outer tube 15. The outer tube is covered by the bottom ring on the front side in such a way that a ring-shaped gap 19 is formed between outer tube 15 and inner tube 16. Ring-shaped gap 19 is connected to the exhaust gas flow via gas passage apertures 20 present in bottom ring 151. Gas passage apertures 20 are situated circumferentially, which may be equidistantly.

A central protecting tube 21 including tube casing 211 and tube bottom 212 is placed over the gas-side end section 111 of sensor element 11, the central protecting tube being mounted in sensor housing 12 in such a way that it maintains a radial clearance to end section 111, as well as to inner tube 16. Central protecting tube 21 is conically widened at its end 213 facing away from tube bottom 212 for mounting in sensor housing 12 and rests in a largely positively engaged manner on housing shoulder 121 where it is mounted axially non-displaceably due to seal 13. Gas passage apertures 22 are present in tube casing 211 of central protecting tube 21 which, with respect to gas passage apertures 18 in inner tube 16, are positioned offset toward tube bottom 212. It is configured in such a way that—as in the case of inner tube 16—gas passage apertures 22 are situated circumferentially, which may be equidistantly, and form a circumferential aperture ring. The aperture ring of inner tube 16 and the ring of central protecting tube 21 are axially spaced from one another. The position of gas passage apertures 22, as well as their number, shape, and size are varied depending on the technical circumstances predetermined by the exhaust gas. Protecting tube 21 has a thin wall in the sense that its wall thickness is less than the wall thickness of inner tube 16 or outer tube 15 of double protecting tube 14, but in no way more.

When the sensor is installed in the exhaust pipe, the end section of sensor 11, which protrudes into the exhaust pipe, creates a narrowing in the exhaust pipe. Due to this narrowing, the exhaust gas in the area of front hole 17 in inner tube 16 is accelerated and generates a partial vacuum in this area. At the same time, an overpressure builds up over gas passage apertures 20 in bottom ring 151 of outer tube 15 upstream from the protruding end of inner tube 16 viewed in the flow direction (arrow 23) of the exhaust gas. The pressure gradient created in this way together with the pressure pulsation of the exhaust gas produce an exhaust gas flow within the protecting tubes. This exhaust gas flow enters via some gas passage apertures 20 in bottom ring 151 of outer tube 15 and flows through ring-shaped gap 19 between outer and inner tubes 15, 16 and enters ring gap 24 between inner tube 16 and central protecting tube 21 via gas passage apertures 18 in inner tube 16. In this ring gap 24, the exhaust gas flows in the direction opposite to the flow direction in ring-shaped gap 19 and enters the interior of central protecting tube 21 via gas passage apertures 22 in central protecting tube 21. The separation edges, formed by gas passage apertures 22 in central protecting tube 21, together with the effect of the pulsation of the exhaust gas, create a strong turbulence of the exhaust gas around end section 111 of sensor element 11 in the gas space, whereby the exhaust gas is exchanged sufficiently quickly. The exhaust gas escapes from the interior of central protecting tube 21 via the other part of gas passage apertures 22 and via front hole 17 of inner tube 16. Using central protecting tube 21, the heat loss of sensor element 11 due to convection and radiation is reduced in such a way that the specified operating temperature of sensor element 11 is maintained under all operating conditions. Gas passage apertures 18 in inner tube 16 and gas passage apertures 20 in bottom ring 151 of outer tube 15 are designed to be large enough so that they cannot be clogged by depositing particulates such as soot. The particulates which pass through these relatively large gas passage apertures 18, together with the exhaust gas are combusted on the exterior wall of central protecting tube 21, since, because of its proximity to heated sensor element 11 and its thin wall, central protecting tube 21 is heated by the heater of sensor element 11 to a temperature at which these particulates are combusted.

What is claimed is:

1. A sensor, comprising:
   a sensor element which protrudes with a gas-side end section, which is exposed to the measuring gas, from a sensor housing;
   a double protecting tube, which encloses the gas-side end section, and includes an outer tube and an inner tube provided with gas passage apertures, which is enclosed by the outer tube with a radial clearance and which protrudes beyond the free end of the outer tube; and
   a cup-shaped central protecting tube which includes a tube casing provided with gas passage apertures and a tube bottom placed over the gas-side end section of the sensor element, and which is positioned with radial clearance from the gas-side end section and from the inner tube, wherein all of the gas passage apertures in the tube casing are positionedly offset toward the tube bottom with respect to the gas passage apertures in the inner tube.

2. The sensor of claim 1, wherein the central protecting tube is mounted on the sensor housing.

3. A sensor comprising:
   a sensor element which protrudes with a gas-side end section, which is exposed to the measuring gas, from a sensor housing;

a double protecting tube, which encloses the gas-side end section, and includes an outer tube and an inner tube provided with gas passage apertures, which is enclosed by the outer tube with a radial clearance and which protrudes beyond the free end of the outer tube; and a cup-shaped central protecting tube which includes a tube casing provided with gas passage apertures and a tube bottom placed over the gas-side end section of the sensor element, and which is positioned with radial clearance from the gas-side end section and from the inner tube, wherein the gas passage apertures in the tube casing are positionedly offset toward the tube bottom with respect to the gas passage apertures in the inner tube, wherein the central protecting tube is mounted on the sensor housing, wherein an end of the central protecting tube facing away from the tube bottom is conically widened and rests between a housing shoulder formed in the sensor housing and a ceramic seal.

4. The sensor of claim 3, wherein the protruding end of the inner tube of the double protecting tube is conically tapered.

5. The sensor of claim 3, wherein the protruding end of the inner tube is terminated by a tube bottom, and at least one front hole is situated in the tube bottom.

6. The sensor of claim 1, wherein the tube bottom is in one piece with the inner tube.

7. The sensor of claim 3, wherein the outer tube rests outside on the inner tube via a bottom ring, and the bottom ring includes gas passage apertures which are positionedly offset with respect to one another in a circumferential direction.

8. The sensor of claim 3, wherein the gas passage apertures in the inner tube of the double protecting tube and the gas passage apertures in the tube casing of the central protecting tube are distributed in a ring shape over the tube circumference, and the aperture rings in the inner tube and the central protecting tube are spaced axially from one another.

9. The sensor of claim 8, wherein the gas passage apertures in the inner tube of the double protecting tube and the gas passage apertures in the tube casing of the central protecting tube are distributed equidistantly in the ring shape over the tube circumference.

10. The sensor of claim 3, wherein the central protecting tube includes a thin wall.

11. The sensor of claim 10, wherein a wall thickness of the central protecting tube is no greater than a wall thickness of the double protecting tube.

12. The sensor of claim 3, wherein the sensor element rests on an interior wall of the sensor housing via a gapless enclosing seal, and the central protecting tube is fixed with its conically widened end by a seal in an axially nonshiftable manner on a housing shoulder.

13. The sensor of claim 3, wherein the sensor includes a gas sensor for determining a physical characteristic of a measuring gas.

14. The sensor of claim 13, wherein the physical characteristic includes a temperature or a concentration of a gas component.

15. The sensor of claim 14, wherein the gas component includes the exhaust gas of an internal combustion engine.

16. The sensor of claim 3, wherein the central protecting tube is mounted on the sensor housing in a positively engaged manner.

* * * * *